US009743903B1

(12) United States Patent
Hall et al.

(10) Patent No.: US 9,743,903 B1
(45) Date of Patent: Aug. 29, 2017

(54) TRENDING USER FEEDBACK BASED ON TOILET NOISE DETECTION

(71) Applicants: David R. Hall, Provo, UT (US); Dan Allen, Springville, UT (US); Ben Swenson, Lehi, UT (US); Joshua Larsen, Spanish Fork, UT (US); Jared Reynolds, Pleasant Grove, UT (US)

(72) Inventors: David R. Hall, Provo, UT (US); Dan Allen, Springville, UT (US); Ben Swenson, Lehi, UT (US); Joshua Larsen, Spanish Fork, UT (US); Jared Reynolds, Pleasant Grove, UT (US)

( * ) Notice: Subject to any disclaimer, the term of this patent is extended or adjusted under 35 U.S.C. 154(b) by 0 days.

(21) Appl. No.: 15/176,501

(22) Filed: Jun. 8, 2016

(51) Int. Cl.
*A61B 7/00* (2006.01)
*E03D 9/00* (2006.01)
*A61B 5/00* (2006.01)
*H04R 1/02* (2006.01)

(52) U.S. Cl.
CPC ............ *A61B 7/008* (2013.01); *A61B 5/0002* (2013.01); *A61B 5/486* (2013.01); *A61B 5/6891* (2013.01); *A61B 5/7275* (2013.01); *A61B 5/7405* (2013.01); *E03D 9/00* (2013.01); *H04R 1/028* (2013.01)

(58) Field of Classification Search
CPC ............ A61B 5/486; A63B 2071/0625; A63B 2230/00
See application file for complete search history.

(56) References Cited

U.S. PATENT DOCUMENTS

| 7,194,776 | B1 * | 3/2007 | Lastuka | E03D 13/00 340/603 |
| 8,331,577 | B2 * | 12/2012 | Lyon | G10K 11/178 181/206 |
| 9,497,558 | B1 * | 11/2016 | Millikin | H04R 29/00 |
| 2004/0155779 | A1 * | 8/2004 | Ballard | G08B 3/10 340/573.1 |
| 2006/0039569 | A1 * | 2/2006 | Antaki | G10K 11/1788 381/71.1 |
| 2008/0082022 | A1 * | 4/2008 | Brohan | A61B 5/208 600/573 |

* cited by examiner

*Primary Examiner* — Mohammad Islam

(57) ABSTRACT

One or more microphones and a controller are used to detected, transmit, and store toilet noise data. One or more speakers are used to provide user feedback based on the detected toilet noise data. Speakers, microphones, and circuitry may be located within a toilet seat of a toilet. A user device or remote device may be connected to the toilet noise detection toilet apparatus for data recording, collection, and health trend reporting.

18 Claims, 10 Drawing Sheets

TRENDING USER FEEDBACK BASED ON TOILET NOISE DETECTION

BACKGROUND

Field of the Invention

This invention relates to methods and systems for collecting and reporting toilet noise data.

Background of the Invention

Attempts have been made to mask toilet noise using music and white noise. Both of these methods create additional noise and do utilize the opportunity of detecting and storing noise created by a user using a toilet.

SUMMARY

One or more microphones and a controller are used to detected, transmit, and store toilet noise data. One or more speakers are used to provide user feedback based on the detected toilet noise data. Speakers, microphones, and circuitry may be located within a toilet seat of a toilet. A user device or remote device may be connected to the toilet noise detection toilet apparatus for data recording, collection, and health trend reporting.

Information which is recorded and reported may include noises from within the toilet including bowel movements, bowel movement frequency, urination duration, urination frequency, user speech, user commands, flatulence, etc. The information may be used to provide medical data to doctors, tracking of digestive health, tracking of urinary system health, and/or hydration information. Such communication signals may be transmitted and stored by way of Internet transmission. Collected user data may be provided to a user's doctor or may be kept for recording trends in the user's health related to noises obtained from microphones on the toilet. Speakers on the toilet may give users of the toilet feedback based on noises recorded. User feedback may include a liquid volume amount or amount of urination, frequency of urination within a given time frame, frequency of bowel movements within a given time frame, constipation information (based on bowel movement plopping noises and size of bowel movement noise information), etc. A user may be identified by voice recognition with in a toilet controller or in a remote database server. A user account and profile may be kept and recorded toilet noises may be stored and associated with a user profile. User health trends may be reported based on stored data collected from toilet noises created by the user using the toilet.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, may be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings.

Figure 1:
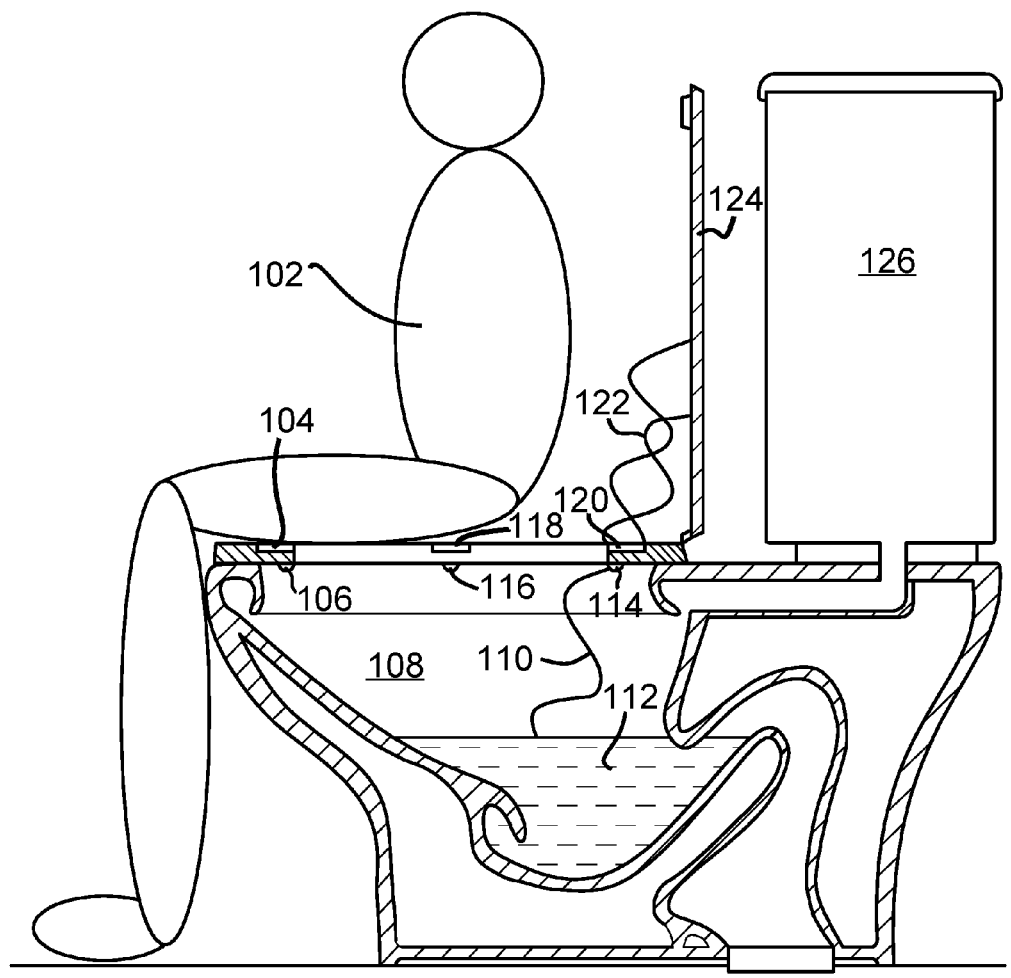
FIG. 1 is a side view of a toilet in accordance with an embodiment of the invention.
Figure 4:
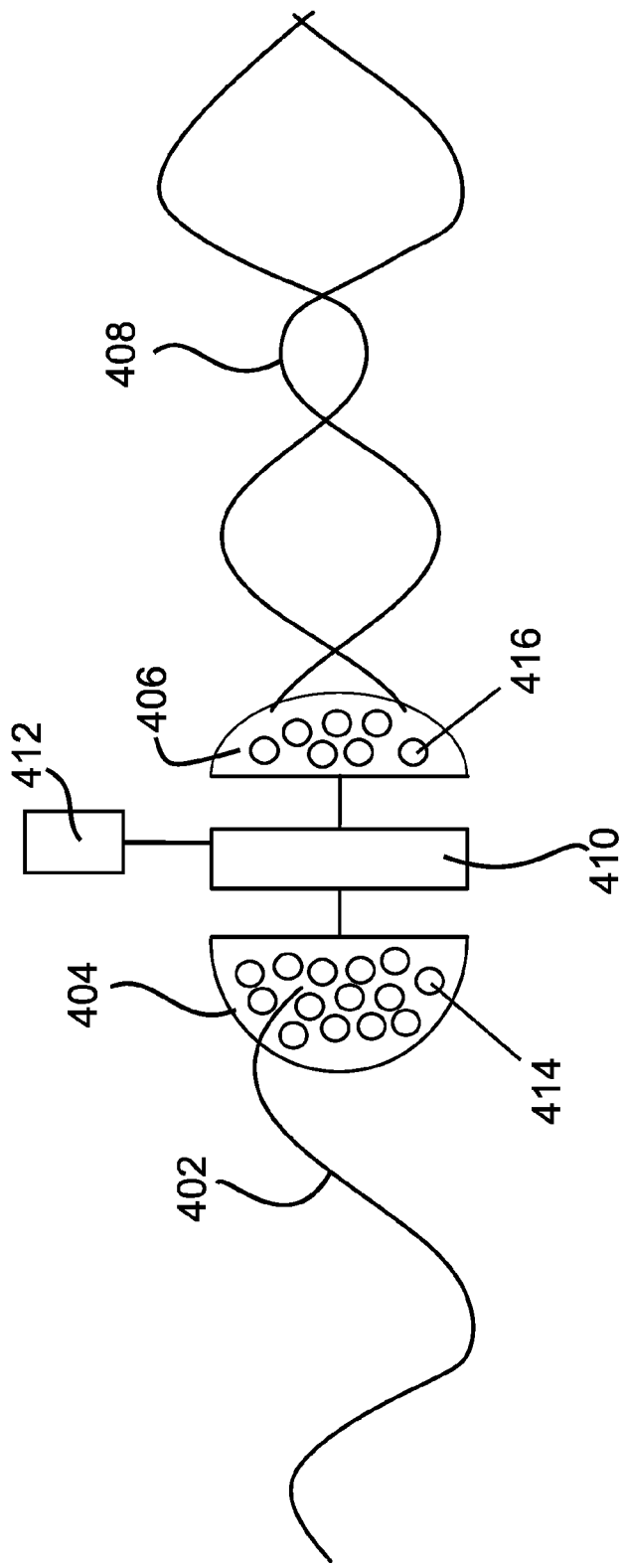
FIG. 4 is a diagram of sound and inverted sound in accordance with an embodiment of the invention.

FIG. 1 shows a cross-sectional view of a user 102 sitting on a toilet. Noise 110 which radiates from an inside bowl area 108 are received by one or more microphones 106 and 114. Microphones 106 and 114 may be a single microphone or may comprise an array of microphones (as shown in FIG. 4) pointed in different directions. Circuitry connected to microphones 106 and 114 may transmit or record sound waves 110. The speakers 116, 118, 104 and 120 may each comprise an array of speakers (as shown in FIG. 4) pointed in different directions. The speakers may provide user feedback based on recorded noises 110. Additional microphones may be located on a toilet lid 124, on toilet tank 126, or at a remote location such as a bathroom door. Additional speakers may also be located on lid 124, on toilet tank 126, or at a remote location such as a bathroom door. Microphones 106 and 114 may be located on or in a toilet seat as shown in FIG. 1. Microphones 106 and 114 may receive in multiple directions including from the bowl and toward a user or a lid of the toilet. Lid 124, the toilet seat, or an inside of the toilet may be made of sound absorptive material such as mass loaded vinyl, high density material, anechoic material, or geometric sound canceling formations. Toilet sound 110 is radiated from a bowl area 108 and received by microphone 114. Microphone 114 provides toilet sound wave signals to circuitry (not shown). The circuitry may transmit or store the toilet sound wave signals. One or more speakers may provide user feedback. User feedback may include a volume or amount of urination, frequency of urination within a given time frame, frequency of bowel movements within a given time frame, constipation information (based on bowel movement plopping noises and size of bowel movement noise information), etc. User feedback may be determined from predetermined/prerecorded sound patterns compared to toilet noises picked up by toilet microphones while a user is using a toilet. For instance, a toilet user may be constipated and the user may make sounds that match prerecorded noises of toilet users who are constipated, such as groaning or grunting noises picked up toilet microphones. In another example, a urination noise length and urination noise harmonics may match a predetermined condition of urinary retention or dehydration or bladder infection. User feedback may be based on a match of a prerecord noise pattern of toilet noise medical conditions.

Figure 2A:
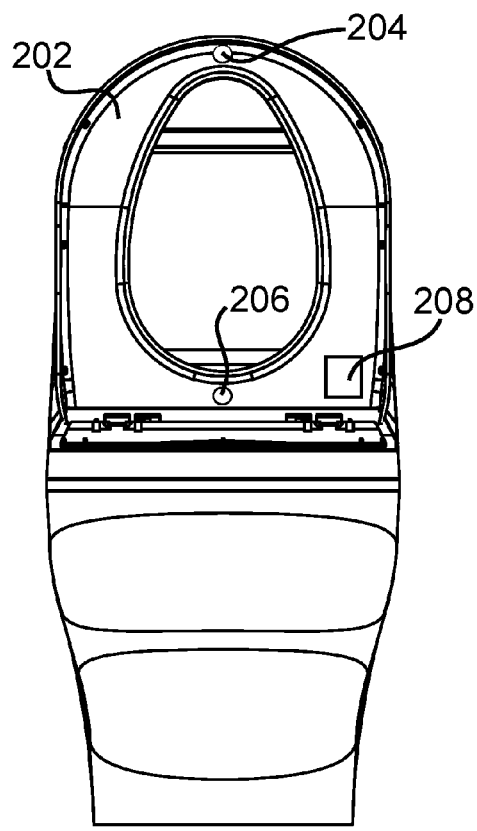
FIG. 2a is a bottom view of a toilet seat in accordance with an embodiment of the invention.
Figure 2B:
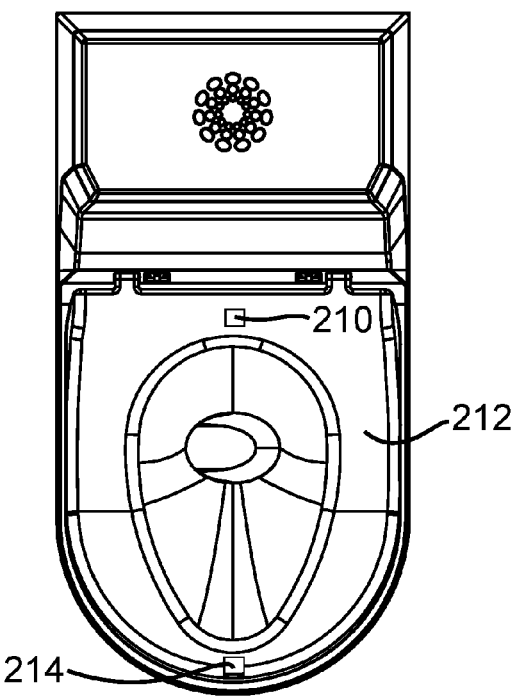
FIG. 2b is a top view of a toilet seat in accordance with an embodiment of the invention.

FIGS. 2a and 2b show a bottom side 202 of a toilet seat and a top side of a toilet seat 212. Shown at 204 and 206 are combination microphone speaker arrays which may be used to receive sound waves and transmit user feedback. One or more speakers may provide user feedback. User feedback may include a volume or amount of urination, frequency of urination within a given time frame, frequency of bowel movements within a given time frame, constipation information (based on bowel movement plopping noises and size of bowel movement noise information), etc.

Figure 3:
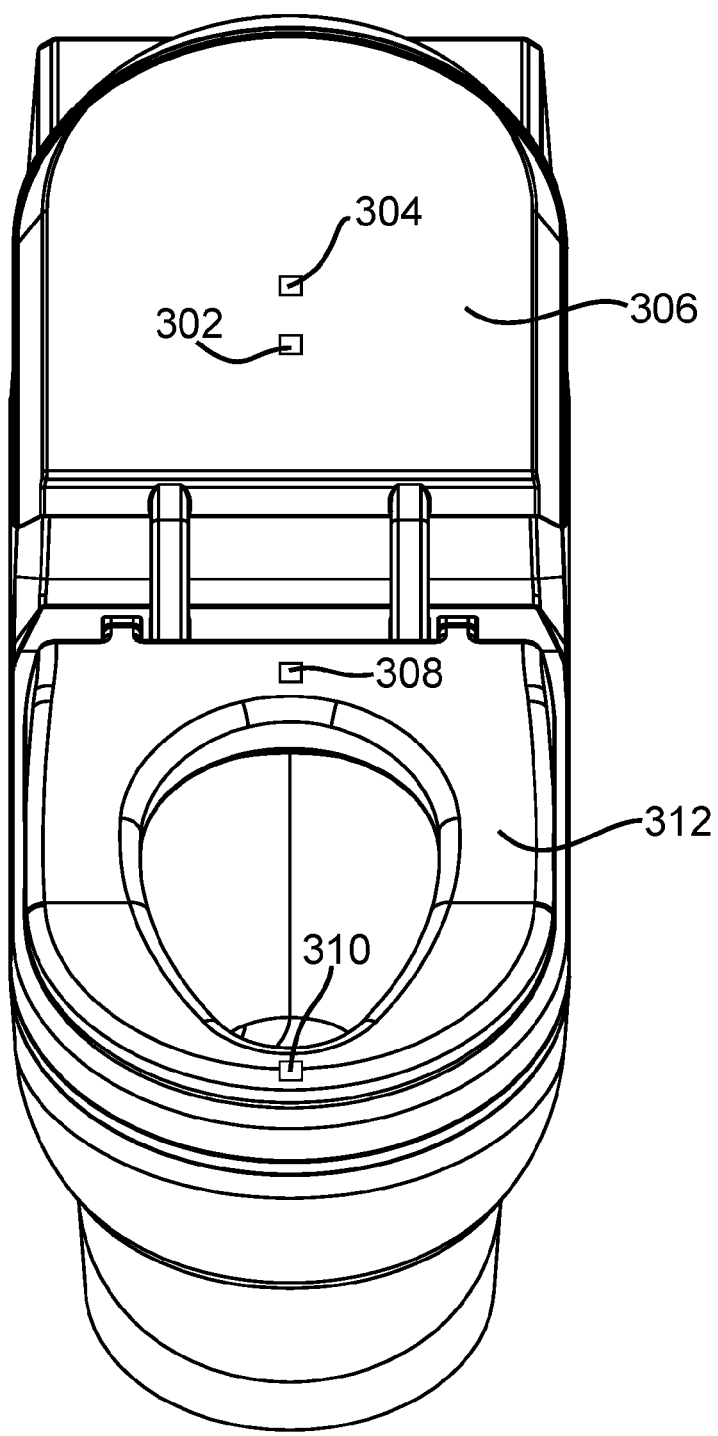
FIG. 3 is a perspective view of a toilet seat in accordance with an embodiment of the invention.

Referring now to FIG. 3, combination microphone speaker arrays 302, 304, 306 and 308 may be used to transmit sound waves and receive sound waves. One or more speakers may provide user feedback. User feedback may include a volume or amount of urination, frequency of urination within a given time frame, frequency of bowel movements within a given time frame, constipation information (based on bowel movement plopping noises and size of bowel movement noise information), etc. The circuitry may be powered by a battery, by a power supply with the toilet, or by a non-contact inductive power source within the toilet seat and another fixed part or the toilet such as the toilet tank, or toilet bowl. The speakers and microphones may be placed adjacent to each other in arrays or be separate arrays which may be spherical or hemispherical arrays of speakers and/or microphones. The microphones and/or speakers 302, 304 may be positioned on a lid 306 of a toilet seat 312 as shown in FIG. 3 and provide feedback to one or more circuits associated with microphone and/or speakers.

FIG. 4 shows sound waves 402 entering microphone 404. Microphone array 404 provides a sound wave input signal to circuit 410 by way of each microphone 414 of the array 404. Circuit 410 may contain active and passive circuitry which stores or records the sound wave signal. Circuit 410 may also output a user feedback signal to one or more speakers 416 of speaker array 406. Speaker array 406 may provide a toilet user with feedback 408 related to toilet noises 402 received. Circuit 410 may be connected to a computer or remote database 412. Computer 412 may include a battery or power supply for powering circuitry 410.

Figure 5:
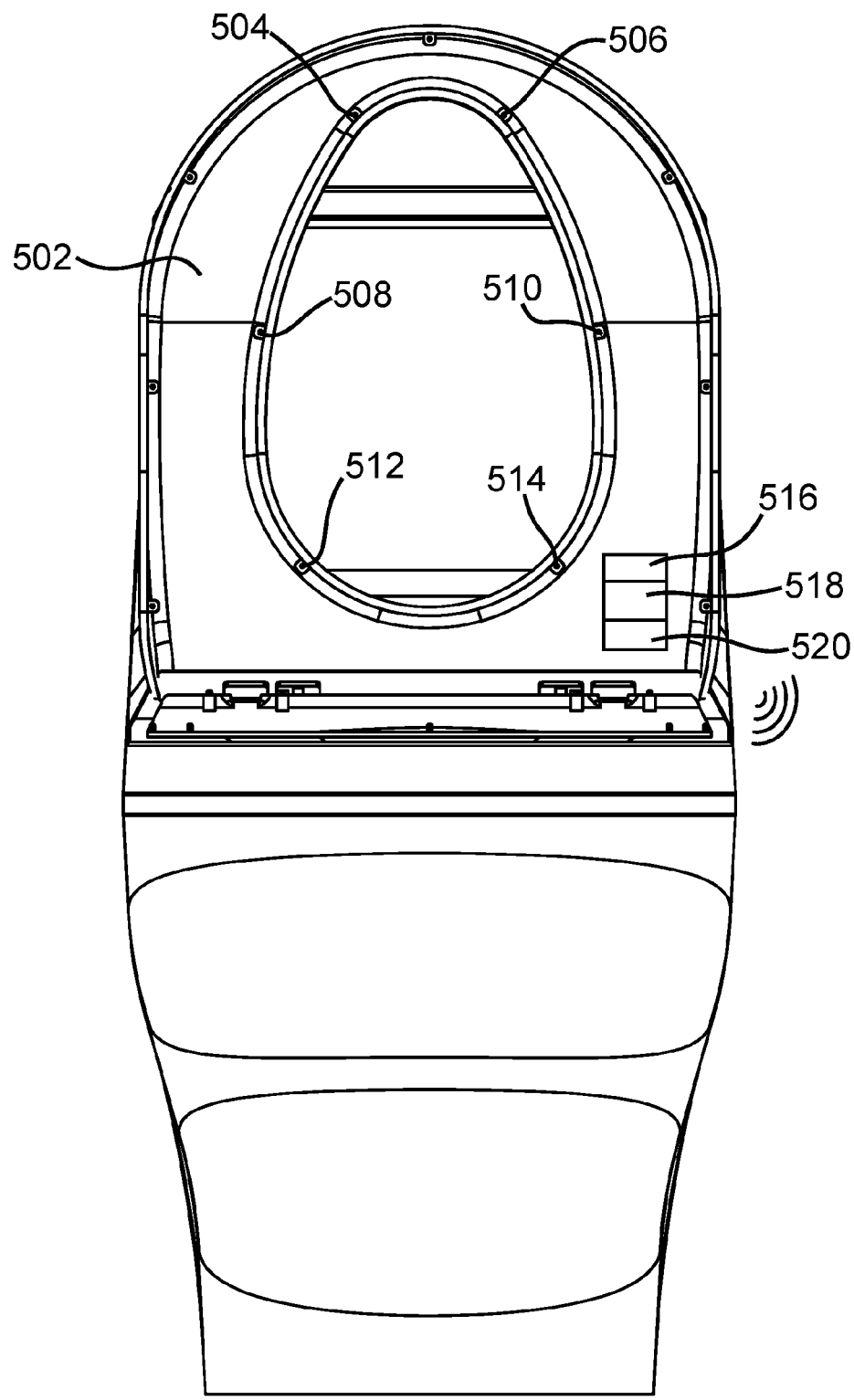
FIG. 5 is a bottom view of a toilet seat in accordance with an embodiment of the invention.

Referring now to FIG. 5, one or more microphones within the arrays 504, 506, 508, 510, 512 and 514 may provide directional information about a propagation path of a sound wave. The microphones may receive different amplitude signals resulting from reception of sound waves. The different amplitude signals may be used to determine a propagation direction of the sound waves. Circuitry 518 may receive one or more microphone input signals with sound wave frequency and direction information. The circuitry may then locally store or transmit the sound wave signals to a remote database for processing. The circuitry may include a processor and be powered by a power source 516. The power source may be a battery, a power supply within the toilet, or a non-contact inductive power source within multiple parts of the toilet such as the toilet seat and another location of the toilet. A communication section 520 may wirelessly transmit information gathered by the microphones to a remote computer or user device. The information transmitted may include noises from within the toilet including bowel movements, bowel movement frequency, urination duration, urination frequency, user speech, user commands, flatulence, etc. The information may be used to provide medical data to doctors, tracking of digestive health, tracking of urinary system health, voice recognition commands, talking on a telephone while in a restroom. Sounds picked up by the microphones may be used to cancel sounds such as urination sounds and amplify wanted sounds such as a user's voice talking to a friend over the Internet through microphones in the toilet. The canceled sounds may be canceled by mixing sound waves in free space or by canceling or filtering out unwanted sound signals in electronic communications. The speakers and microphones may be placed adjacent to each other in arrays or be separate arrays which may be spherical or hemispherical arrays of speakers and/or microphones. The microphones and/or speakers 504, 506, 508, 510, 512 and 514 may be positioned on a toilet seat 502 and provide feedback to one or more circuits associated with microphone and/or speakers. The speakers may be used to transmit desired sounds in addition to inverted unwanted sound waves. For instance, if a user is talking to a friend over the Internet using the microphones and the speakers on the toilet, the microphones and speakers may also be providing noise canceling features while the user is using the toilet. A user may pair the noise canceling toilet to a user device and talk on the telephone hands free without worrying about toilet noises being transmitted through to the other end of the telephone call.

Figure 6:
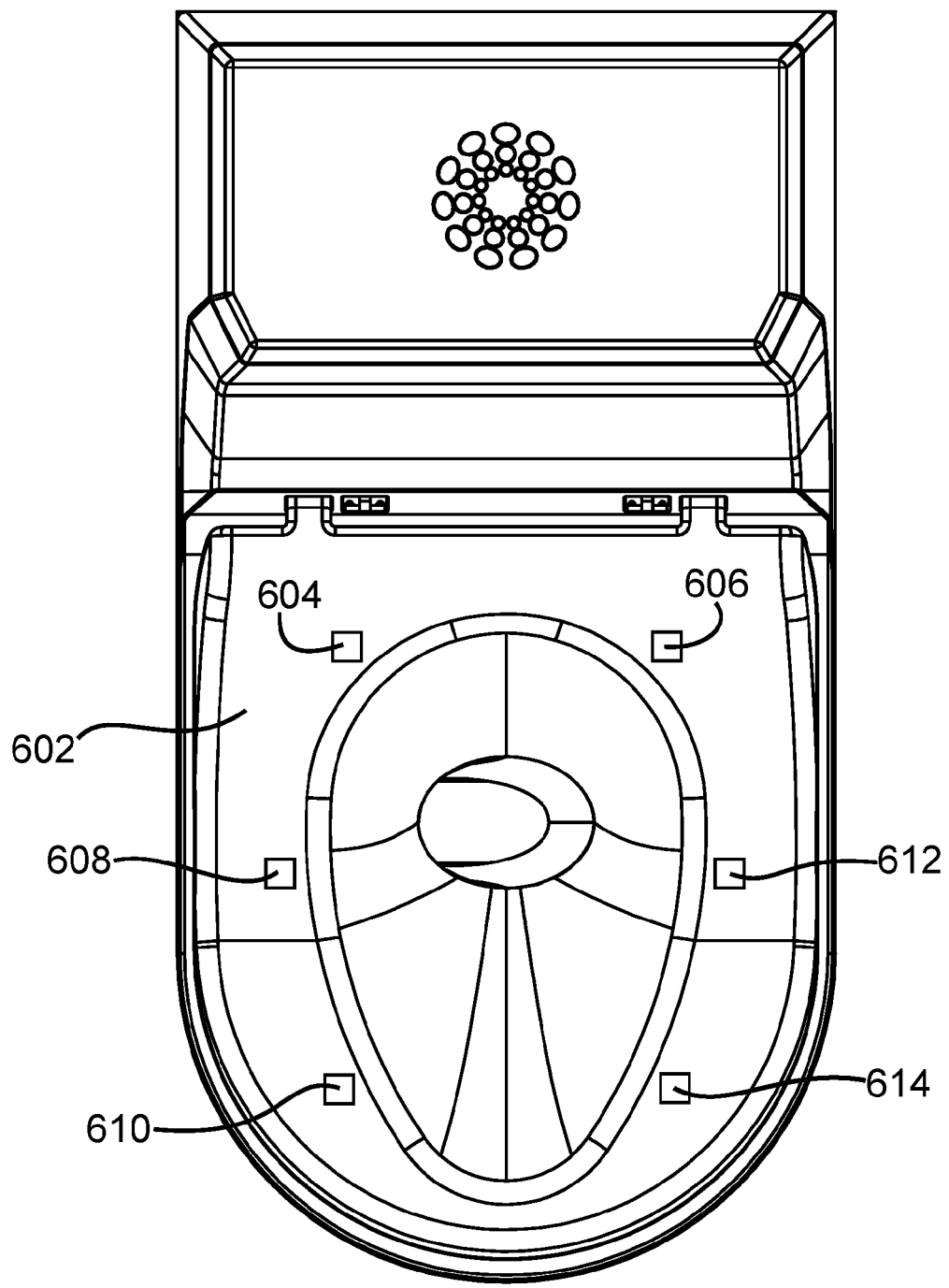
FIG. 6 is top view of a toilet seat in accordance with an embodiment of the invention.

In FIG. 6, combination microphone speaker arrays 604, 606, 608, 610, 612 and 614 may be used to transmit inverted sound waves and receive unwanted sound waves. The speakers may transmit inverted sound waves in an upward direction toward a sound point origin location or reflection location outside of the toilet bowl or to a virtual space. The transmitted inverted sound waves may be transmitted in a propagation direction similar to a reflected unwanted sound reflection path or along a similar propagation directional axis. One or more microphones within the arrays 604, 606, 608, 610, 612 and 614 may provide directional information about a propagation path of an unwanted sound wave. The microphones may receive different amplitude signals resulting from reception of unwanted sound waves. The different amplitude signals may be used to determine a propagation direction of the unwanted sound waves. Circuitry 518, of FIG. 5, may receive one or more microphone input signals with unwanted sound wave frequency and direction information. The circuitry may then invert the received signal and transmit the inverted unwanted sound wave signal to one or more speakers in an array of speakers within 604, 606, 608, 610, 612 and/or 614. The circuitry may be powered by a power source 516 of FIG. 5. The power source may be a battery, a power supply within the toilet, or a non-contact inductive power source within multiple parts of the toilet such as the toilet seat and another location of the toilet. A communication section 520, of FIG. 5, may wirelessly transmit information gathered by the microphones to a remote computer or user device. The information transmitted may include noises from within the toilet including bowel movements, bowel movement frequency, urination duration, urination frequency, user speech, user commands, flatulence, etc. The information may be used to provide medical data to doctors, tracking of digestive health, tracking of urinary system health, voice recognition commands, talking on a telephone while in a restroom. Sounds picked up by the microphones may be used to cancel unwanted sounds such as urination sounds and amplify wanted sounds such as a user's voice talking to a friend over the Internet through microphones in the toilet. The canceled sounds may be canceled by mixing sound waves in free space or by canceling or filtering out unwanted sound signals in electronic communications. The speakers and microphones may be placed adjacent to each other in arrays or be separate arrays which may be spherical or hemispherical arrays of speakers and/or microphones. The microphones and/or speakers 604, 606, 608, 610, 612 and 614 may be positioned on a toilet seat 602 and provide feedback to one or more circuits associated with microphone and/or speakers. The speakers may be used to transmit desired sounds in addition to inverted unwanted sound waves. For instance, if a user is talking to a friend over the Internet using the microphones and the speakers on the toilet, the microphones and speakers may also be providing noise canceling features while the user is using the toilet. A user may pair the noise canceling toilet to a user device and talk on the telephone hands free without worrying about toilet noises being transmitted through to the other end of the telephone call.

Figure 7:
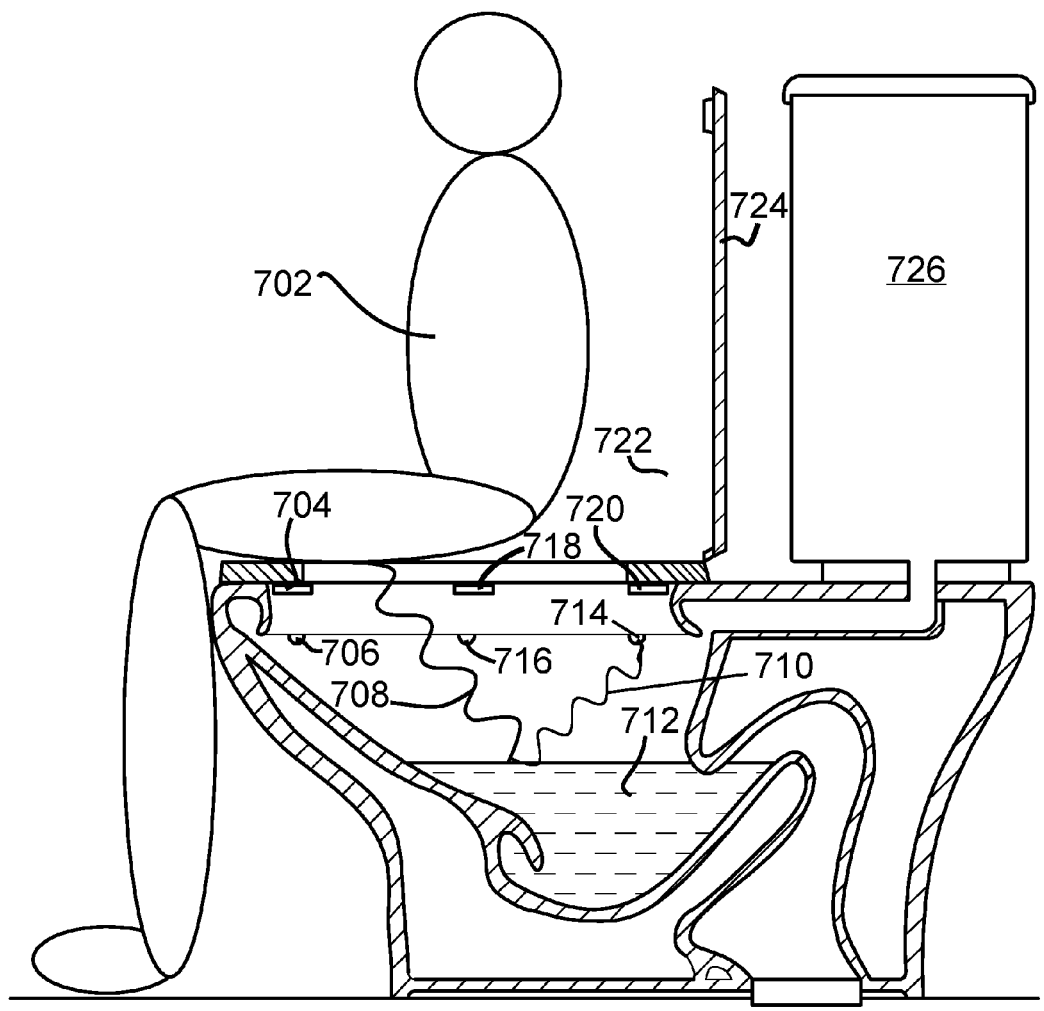
FIG. 7 is a side view of a toilet in accordance with an embodiment of the invention.

In FIG. 7, a cross-sectional view of a user 702 sitting on a toilet. noise or unwanted sound waves 708 which radiate from inside of a bowl area of a toilet 726 are received by one or more microphones 706, 716, 714, 704, 718, and 720. Microphones 706, 716, 714, 704, 718, and 720 may each be a single microphone or may each be an array of microphones pointed in different directions. Circuitry connected to microphones 706, 716, 714, 704, 718, and 720 invert the unwanted noise or unwanted sound waves 708 and output an inverted unwanted sound wave signal to one or more speakers 706, 716, 714, 704, 718, and 720 which transmit the inverted unwanted noise or inverted unwanted sound waves 710. The speakers 706, 716, 714, 704, 718, and 720 may each comprise an array of speakers pointed in different directions. The inverted unwanted sound waves 710 mix or combine with unwanted sound waves to cancel or substantially cancel each other. The speakers may transmit the inverted signal in a similar direction compared to a propagation direction of received unwanted sound waves. The speakers may transmit the inverted signal in a downward direction into the toilet bowl, in an upward direction out of the toilet bowl, or in a combination of directions based on a direction of the unwanted sound radiation. Additional microphones may be located on a toilet lid 724, on toilet tank 726, or at a remote location such as a bathroom door. The additional microphones may provide feedback about noise cancelation in order to calibrate the output of one or more speakers. Additional speakers may also be located on lid 724, on toilet tank 726, or at a remote location such as a bathroom door and may provide additional noise cancelation radiation. Microphones 706, 716, 714, 704, 718, and 720 may be located on or in a toilet seat as shown in FIG. 7. Microphones 706, 716, 714, 704, 718, and 720 may transmit in multiple directions including into the bowl and toward a user or a lid of the toilet. Lid 724, the toilet seat, or an inside of the toilet may be made of sound absorptive material such as mass loaded vinyl, high density material, anechoic material, or geometric sound canceling formations. sound 708 is radiated from a bowl area of a toilet and received by microphone array 716. Microphone array 716 provides an unwanted sound wave signal to circuitry (not shown). The circuitry inverts the unwanted sound wave signal and outputs the inverted unwanted sound wave signal to one or more speakers 714. The speakers may be chosen based on a direction of propagation of the unwanted sound. The direction of propagation may be determined based on an array of microphones which may be located at microphone 716. The array may be formed in a hemispherical or spherical shape and the direction of propagation may be determined based on an intensity received at one or more microphones in the array. Speaker 714 may also comprise an array of speakers forming a hemispherical or spherical shape and one or more of the speakers 714 may be used to transmit the inverted unwanted sound wave signal 714 is a similar direction compared to the propagation direction of the unwanted sound wave 708. If microphone array 716 receives multiple unwanted sound waves which have different propagation directions, then multiple inverted signals may be created and sent to multiple speakers within an array of speakers and the inverted signals may be transmitted by one or more speaker arrays in different propagation directions.

Figure 8:
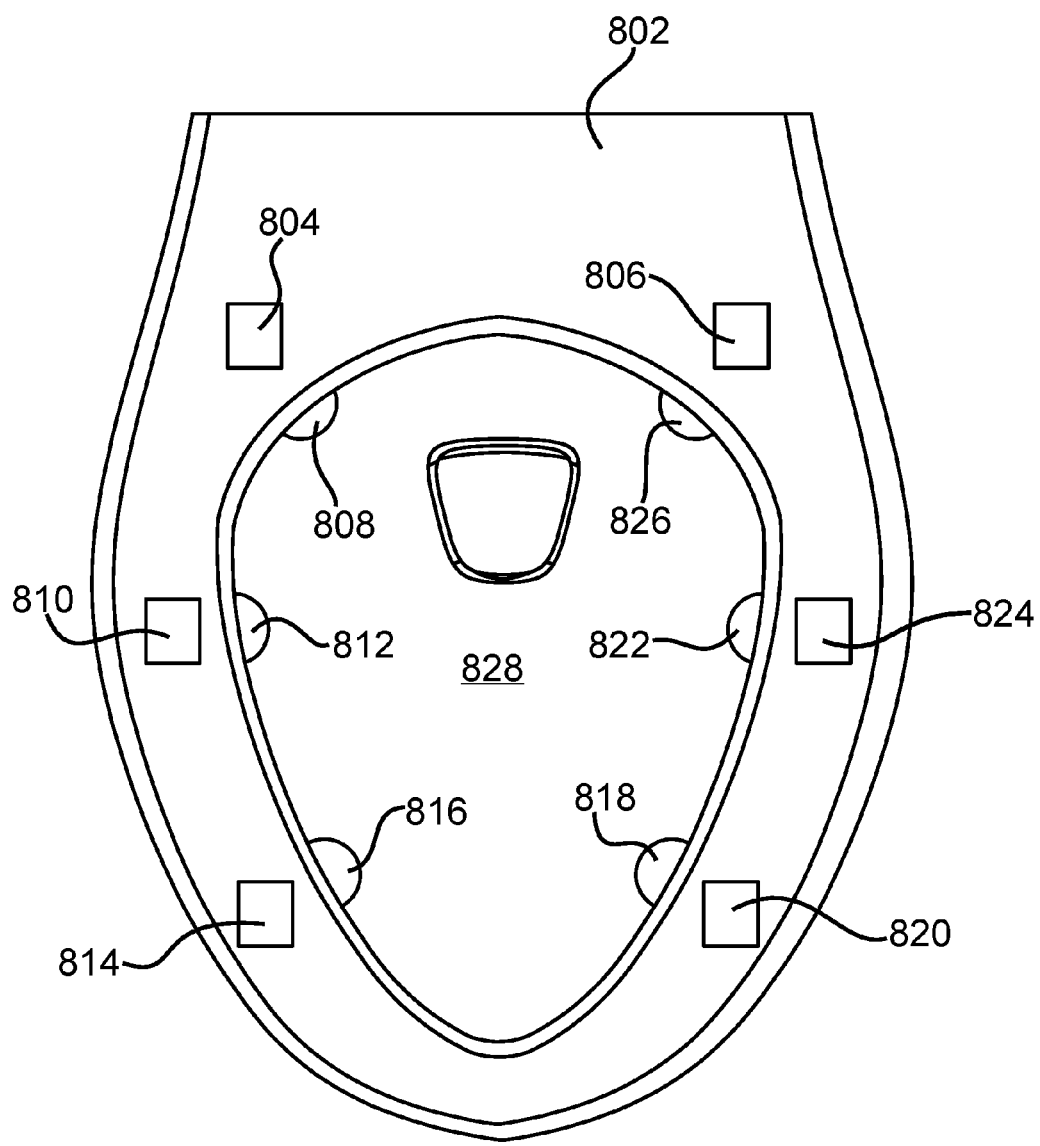
FIG. 8 is a top view of a toilet seat in accordance with an embodiment of the invention.

FIG. 8 shows a toilet seat 802 with speaker microphone combinations 804, 806, 808, 810, 812, 814, 816, 818, 820, 822, 824, and 826. Each speaker microphone combination 804, 806, 808, 810, 812, 814, 816, 818, 820, 822, 824, and 826 contains arrays of both speakers and microphones which may receive and transmit sound waves omni-directionally. The sound waves received and transmitted may be used for both noise cancelation and for audio communications. The noise cancelation may be for both free space noise cancelation and electronic noise cancelation. Free space noise cancelation may include reduction of urination noise, bowel movement noise, flatulence noise, toilet flushing noise, splashing water noise, or other noise generated within toilet bowl 828. Electronic noise cancellation may include audio communications which use the microphones and speakers on the toilet to cancel unwanted noise from a communication signal. Such communication signals may include telephone calls, intercom communications, and Internet transmissions. A toilet apparatus of the current invention may be used as a pairing device for hands free electronic communications without the worry of unwanted toilet noise being present in the electronic communication signal.

Figure 9:
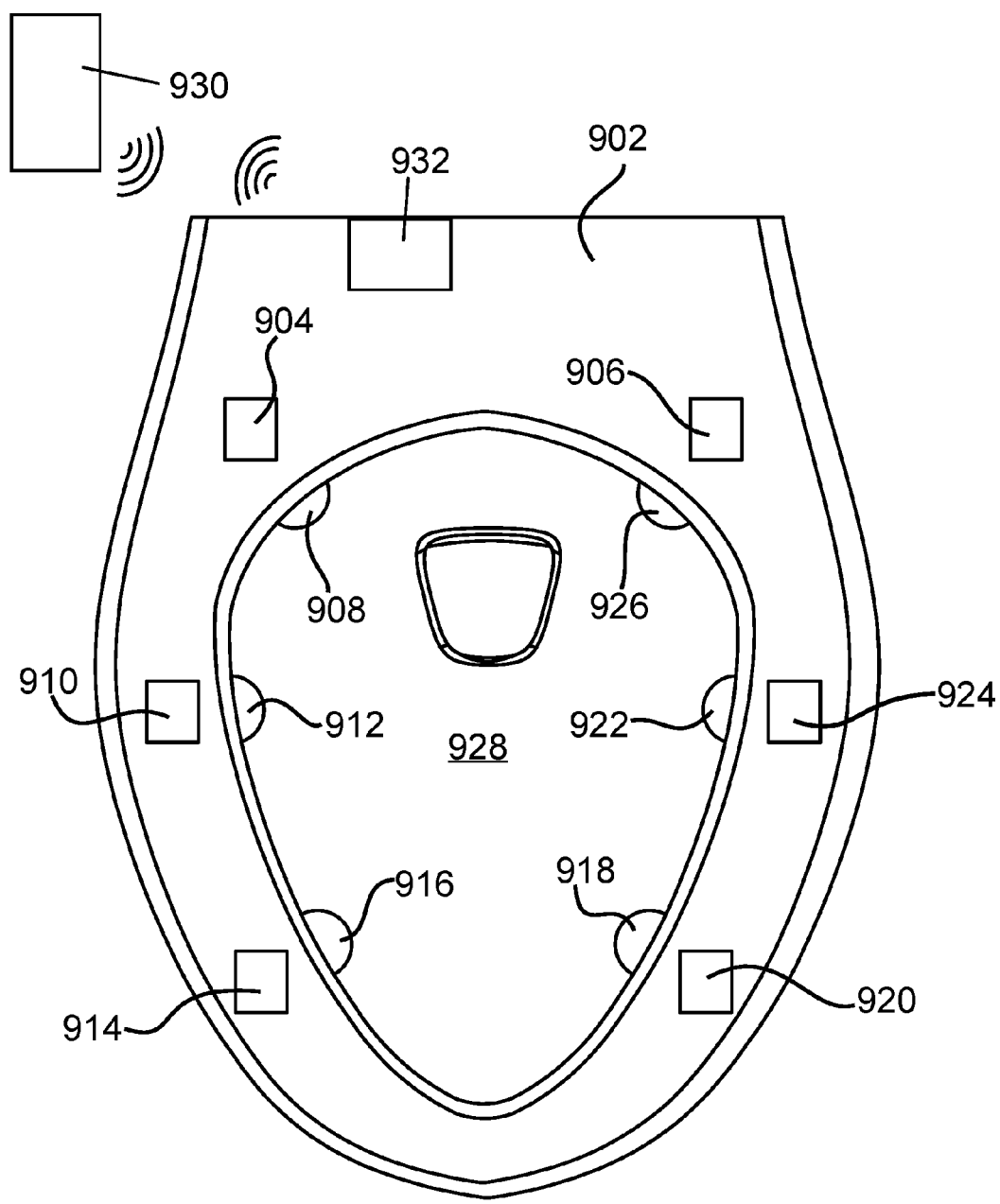
FIG. 9 is a top view of a toilet seat and a user device in accordance with an embodiment of the invention.

In FIG. 9, a user device 930 such as a telephone may be wirelessly connected to toilet seat 902. Toilets seat 902 may have a controller 932 including a processor, memory, a power source, and a wireless communications module. Each speaker microphone combination 904, 906, 908, 910, 912, 914, 916, 918, 920, 922, 924, and 926 contains arrays of both speakers and microphones which may receive and transmit sound waves omni-directionally. The sound waves received and transmitted may be used for both noise cancelation and for audio communications. The noise cancelation may be for both free space noise cancelation and electronic noise cancelation. Free space noise cancelation may include reduction of urination noise, bowel movement noise, flatulence noise, toilet flushing noise, splashing water noise, or other noise generated within a toilet bowl. Electronic noise cancellation may include audio communications which use the microphones and speakers on the toilet to cancel unwanted noise from a communication signal. Such communication signals may include telephone calls, intercom communications, and Internet transmissions. A toilet apparatus of the current invention may be used as a pairing device for hands free electronic communications without the worry of unwanted toilet noise being present in the electronic communication signal. For instance, a toilet user may desire to make a hands free phone call while using the toilet without the other party hearing any unwanted toilet noises. The toilet user may use a Bluetooth connection to connect with toilet controller 932. Toilet controller 932 may provide microphone and speaker functionality for user device 930 while electronically filtering and/or canceling unwanted toilet noises generated while using the toilet. noises that may be filtered include shower noises, hair dryer noises, flushing, and noises radiating from within the toilet bowl 928.

Figure 10:
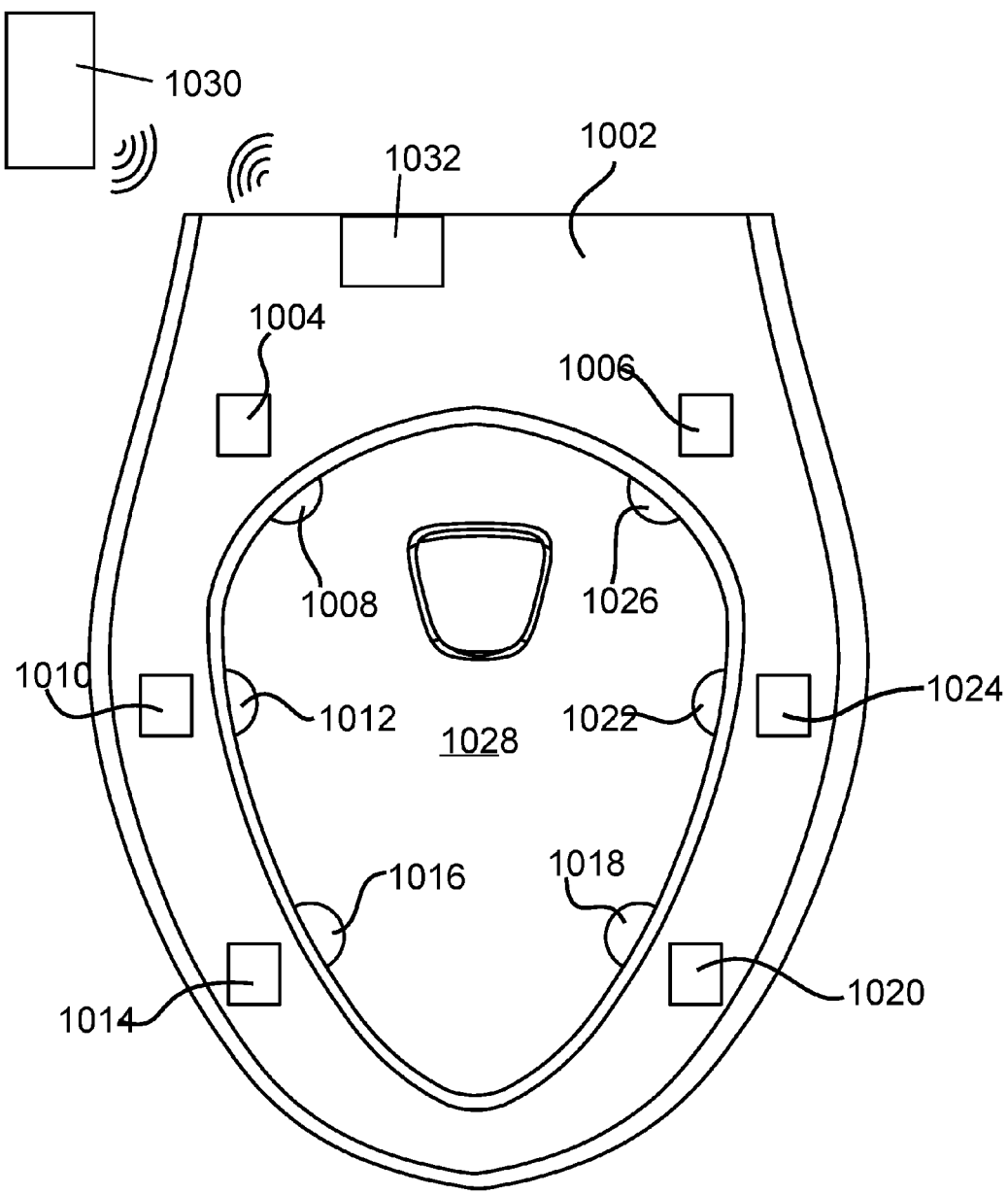
FIG. 10 is a top view of a toilet seat and a remote storage device in accordance with an embodiment of the invention.

In FIG. 10, a remote device 1030 such as a database server or computer may be wirelessly connected to toilet seat 1002 by way of a local or wide area network. Toilets seat 1002 may have a controller 1032 including a processor, memory, a power source, and a wireless communications module. Each speaker microphone combination 1004, 1006, 1008, 1010, 1012, 1014, 1016, 1018, 1020, 1022, 1024, and 1026 contains arrays of both speakers and microphones which may receive and transmit sound waves omni-directionally. The sound waves received and transmitted may be used for both noise cancelation and for toilet data collection. The noise cancelation may be for both free space noise cancelation and electronic toilet noise collection. Free space noise cancelation may include reduction of urination noise, bowel movement noise, flatulence noise, toilet flushing noise, splashing water noise, or other noise generated within a toilet bowl. Electronic noise collection may include audio data picked up by the microphones and speakers while a user is using the toilet. A communication device within controller 1032 may wirelessly transmit information gathered by the microphones to a remote computer or data collection system. The information transmitted may include noises from within the toilet including bowel movements, bowel movement frequency, urination duration, urination frequency, user speech, user commands, flatulence, etc. The information may be used to provide medical data to doctors, tracking of digestive health, tracking of urinary system health, or hydration information. Such communication signals may be transmitted and stored by way of Internet transmissions. Collected user data may be provided to a toilet user's doctor or may be kept for recording trends in the user's health related to noises obtained from microphones on the toilet. Speakers on the toilet may give users of the toilet feedback based on noises recorded. User feedback may include volume of urination feedback, frequency of urination within a given time frame, frequency of bowel movements within a given time frame, constipation information (based on bowel movement plopping noises and size of bowel movement information), etc. A user may be identified by voice recognition with in controller 1032 or my remote voice recognition by a network database server. A user account and profile may be kept and recorded based on toilet noises. User health trends may be reported based on stored data collected from toilet noises created by the user using a toilet.

The toilet and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A toilet apparatus comprising:
   one or more microphones that detect sound waves generated by a user using the toilet apparatus, at least one of the one or more microphones being inside a toilet bowl of the toilet;
   circuitry which filters and transmits data based on the detected sound waves;
   a power supply that powers the circuitry; and
   one or more speakers which give the user feedback based on the detected sound waves.

2. The toilet apparatus of claim 1, wherein at least one of the one or more speakers is located on a lid of a toilet seat of the toilet apparatus.

3. The toilet apparatus of claim 1, wherein all but one of the one or more microphones, the circuitry, the power supply, and the one or more speakers are all attached to a toilet seat of the toilet apparatus.

4. The toilet apparatus of claim 1, wherein the transmitted data is stored in a remote database.

5. The toilet apparatus of claim 1, wherein a shape of the toilet apparatus is configured to direct sound waves in a pattern, direction, or linear path.

6. The toilet apparatus of claim 1, wherein the feedback is audio feedback given through the one or more speakers based on the detected sound waves.

7. The toilet apparatus of claim 1, wherein at least one of the plurality of speakers is attached to a toilet seat of the toilet, a lid of the toilet seat, a toilet bowl of the toilet, or a tank of the toilet.

8. The toilet apparatus of claim 1, wherein at least one of the one or more microphones is used for medical data collection.

9. The toilet apparatus of claim 6, wherein the audio feedback includes trending user data based on the detected sound waves.

10. A method of medical trend reporting comprising:
    detecting sound waves generated by a user using a toilet with one or more microphones, at least one of the one or more microphones being inside a toilet bowl of the toilet;
    providing circuitry which filters and transmits data based on the detected sound waves;
    storing data produced by the detected sound waves; and
    providing user feedback with one or more speakers based on the detected sound waves.

11. The method of claim 10, wherein at least one of the one or more speakers is located on a lid of a toilet seat of the toilet apparatus.

12. The method of claim 10, wherein all but one of the one or more microphones and the one or more speakers are attached to a toilet seat of the toilet apparatus.

13. The method of claim 10, wherein the stored data is stored in a remote database.

14. The method of claim 10, wherein a shape of the toilet is configured to direct sound waves in a pattern, direction, or linear path.

15. The method of claim 10, wherein the feedback is audio feedback given through the one or more speakers based on the detected sound waves.

16. The method of claim 10, wherein at least one of the plurality of speakers is attached to a toilet seat of the toilet, a lid of the toilet seat, a toilet bowl of the toilet, or a tank of the toilet.

17. The method of claim 10, wherein at least one of the one or more microphones is used for medical data collection.

18. The method of claim 15, wherein the audio feedback includes trending user data based on the detected sound waves.

* * * * *